United States Patent [19]

Bobo, Jr. et al.

[11] Patent Number: 4,979,940
[45] Date of Patent: Dec. 25, 1990

[54] INFUSION SYSTEM, METHODOLOGY, AND ALGORITHM FOR IDENTIFYING PATIENT-INDUCED PRESSURE ARTIFACTS

[75] Inventors: Donald E. Bobo, Jr., Orange; Edward F. Meier, Anaheim Hills; Dennis R. Seguine; Theodore R. Lapp, both of Mission Viejo, all of Calif.

[73] Assignee: Baxter International Inc., Deerfield, Ill.

[21] Appl. No.: 369,801

[22] Filed: Jun. 22, 1989

Related U.S. Application Data

[63] Continuation-in-part of Ser. No. 165,619, Mar. 8, 1988, Pat. No. 4,846,792.

[51] Int. Cl.$^5$ ............................................. A61M 31/00
[52] U.S. Cl. ........................................ 604/50; 604/67; 128/DIG. 5
[58] Field of Search ...................... 604/49, 50, 65–67, 604/118, 245, 246; 128/DIG. 12, DIG. 13, 681

[56] References Cited

U.S. PATENT DOCUMENTS

| | | | |
|---|---|---|---|
| 4,140,110 | 2/1979 | Jansen et al. | 128/681 |
| 4,392,847 | 7/1983 | Whitney et al. | 604/118 |
| 4,468,219 | 8/1984 | George et al. | 604/66 |
| 4,551,133 | 11/1985 | Zegers deBeyl et al. | 604/66 |
| 4,657,529 | 4/1987 | Prince et al. | 604/66 |
| 4,710,163 | 12/1987 | Butterfield | 604/65 |

Primary Examiner—Stephen C. Pellegrino
Attorney, Agent, or Firm—Paul E. Schaafsma; Paul C. Flattery; Bradford R. L. Price

[57] ABSTRACT

An infusion system includes fluid-delivery components for delivering a fluid from a separate source of the fluid into a patient, transducer components for producing a signal related to the pressure of the fluid in the fluid-delivery components, and identification components responsive to the signal for identifying pressure artifacts characteristic of patient activity. Gravity-fed infusion may be employed as well as infusion with a flow control device, and identification may be accomplished with a microprocessor for examining the waveform of the signal and identifying pressure artifacts characteristic of patient activity amidst pressure changes caused by fluid-delivery components so that site checking can be conducted during quiet periods, i.e., times of little patient acitivity. A method of detecting an abnormal infusion condition includes infusing a fluid into a patient through a conduit, with the pressure of the fluid in the conduit being subject to influence by patient activity, monitoring the fluid pressure in the conduit in order to detect pressure artifacts characteristic of patient activity, and performing a site check for abnormal infusion conditions at a time when no such pressure artifacts are detected.

27 Claims, 11 Drawing Sheets

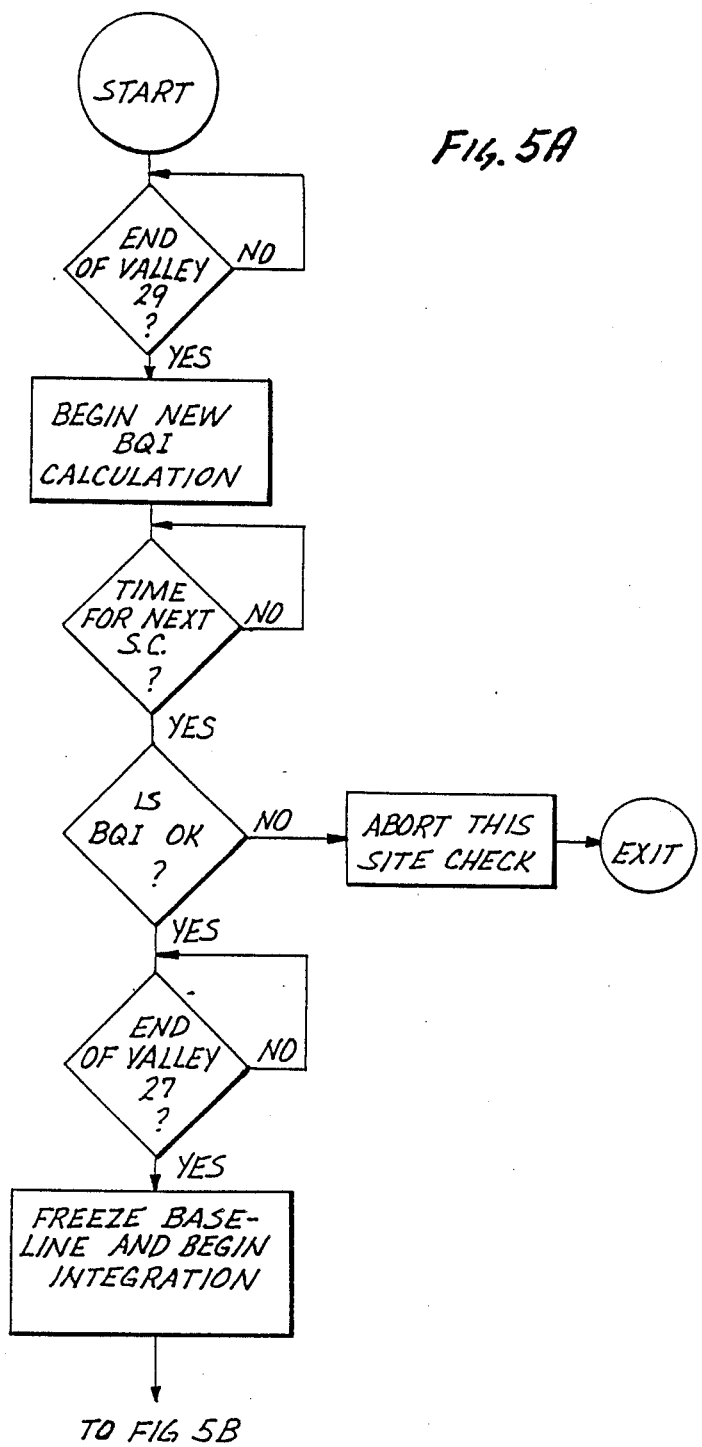

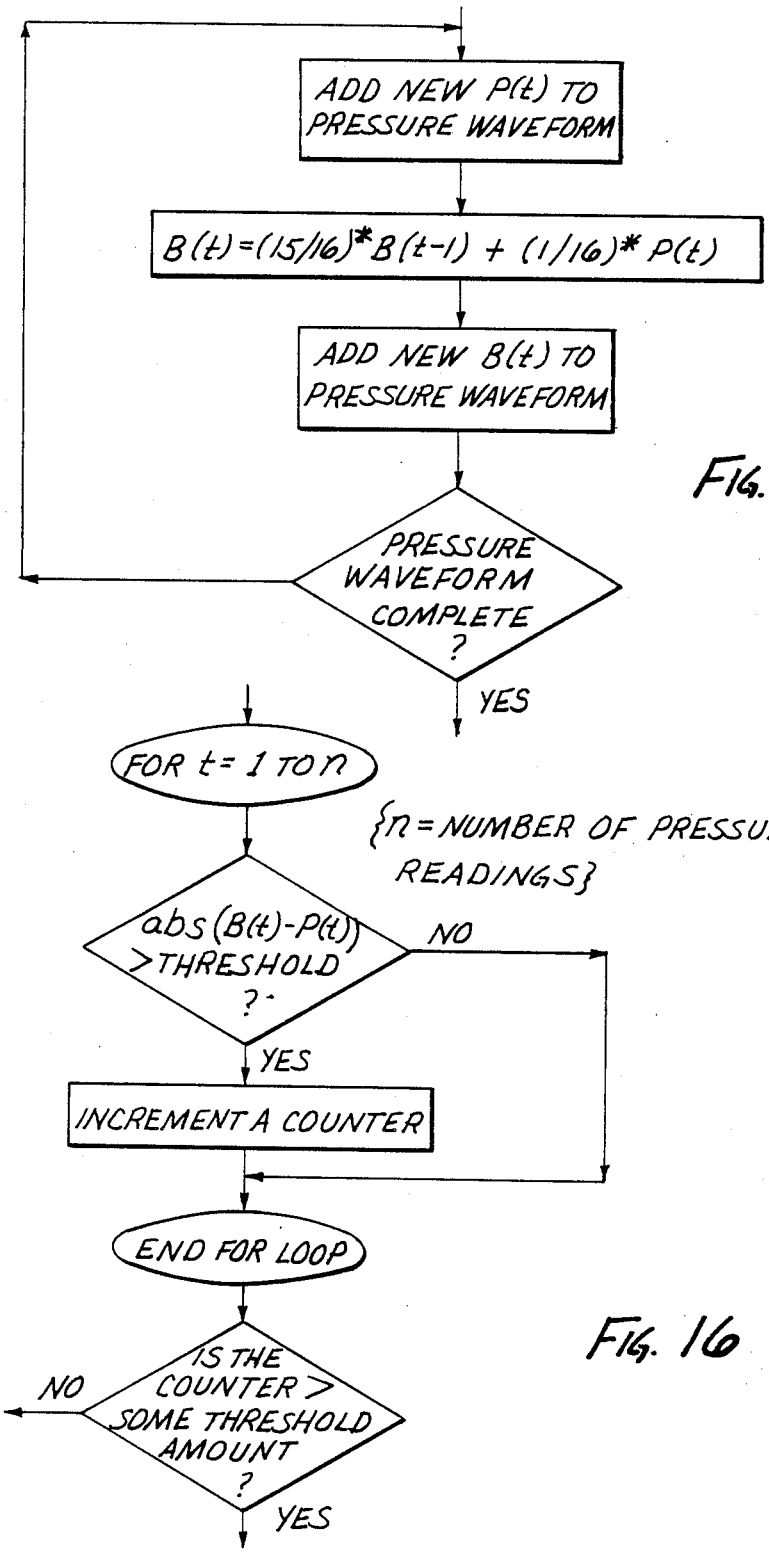

```
                    ↓
        ┌─────────────────────────────┐
        │ DIVIDE THE PRESSURE WAVEFORM INTO │
        │ CYCLES BASED ON LOW POINTS IN THE │
        │ CURVE (MINIMUM P(t)'S)      │
        └─────────────────────────────┘
                    ↓
        ┌─────────────────────────────┐
        │ FOR EACH UNIT, COUNT THE NUMBER │
        │ OF TIMES THAT THE PRESSURE  │
        │ CURVE INTERSECTS THE BASELINE │
        └─────────────────────────────┘
                    ↓
               ╱ NUMBER ╲
              ╱ OF COUNTS < ╲ ── NO ──→
              ╲ THRESHOLD   ╱
               ╲    ?    ╱        FIG. 17
                  YES
                   ↓
```

FIG. 19

```
         ↓                              ↓
    ╱ TIME TO ╲                   ╱ TIME TO ╲
   ╱ DO A SITE CHECK ╲── NO ──→  ╱ DO A SITE CHECK ╲── NO ──→
    ╲    ?    ╱                   ╲    ?    ╱
       YES                     FIG. 20  YES
        ↓                              ↓
   ┌─────────┐                    ╱ DELAY ╲
   │ DO A SITE│                  ╱ TIMER > 5 MIN. ╲── NO ──→
   │  CHECK  │                    ╲    ?    ╱
   └─────────┘                       YES
        ↓                              ↓
                                  ┌─────────┐
                                  │ DO A SITE│
                                  │  CHECK  │
                                  └─────────┘
                                       ↓
```

INFUSION SYSTEM, METHODOLOGY, AND ALGORITHM FOR IDENTIFYING PATIENT-INDUCED PRESSURE ARTIFACTS

CROSS REFERENCE TO RELATED APPLICATION

This application is a continuation-in-part of U.S. Patent. application Ser. No. 165,619 filed Mar. 8, 1988, from which issued U.S. Pat. No. 4,846,792.

BACKGROUND OF THE INVENTION

1. Technical Field

The invention relates generally to medical equipment, and more particularly to an infusion system that operates to introduce fluid into a patient.

2. Background Information

It is often necessary or desirable to infuse a flowable material or fluid, which may be a liquid, a gas, or a combination thereof, into a patient. One example is the administration of parenteral fluids to a patient.

A typical infusion system includes an infusion device (or flow control device) for delivering the fluid and conduit means for conducting the flowable material from the infusion device to the patient. The conduit means typically comprises flexible tubing leading from the infusion device and a cannula, such as a needle or catheter, for insertion into the vascular system of the patient. In normal operation, the infusion device delivers the fluid through the tubing and the needle to the vascular system of the patient.

One problem with infusion systems of that type is a condition known as infiltration. Infiltration is a condition in which infused fluid finds its way into extravascular tissues rather than simply being released into the blood stream. Such a situation occurs when the needle is not in communicator with the interior of the vessel into which the fluid is to be infused. When that occurs, fluid is infused into the interstitial spaces between layers of tissues. Thus, the patient is deprived of proper intravenous drug administration and is further subjected to possible toxic or caustic effects associated with infused fluids being in direct contact with body tissues.

Infiltration is not the only possible type of anomaly associated with intravenous therapy which can cause the fluid to be improperly supplied to the patient. Other conditions which can cause abnormal infusion, i.e., the fluid to be improperly supplied to the patient, include venous inflammation and swelling at the infusion site (phlebitis), clotting, and a wide variety of obstructions of the conduit means, such as kinking of the tubing which supplies the fluid to the patient. Many of these affect fluid flow characteristics in a manner similar to infiltration and can, therefore, be detected by infiltration detection devices.

The goal of an infiltration detection system is to identify an abnormal infusion condition as early as possible without generating an excessive number of false alarms. Early detection allows the attending medical staff to rectify the problem before significant damage has been done by the infiltration and before the patient has been deprived of a significant amount of the intravenous therapy. On the other hand, if the detection system is too sensitive, false alarms will result. That is very undesirable since, from a clinical perspective, establishing a new intravenous site can be difficult and time consuming. During the time necessary to start the new IV, which can be hours in some cases, the patient is not receiving the desired treatment.

Bobo U.S. Pat. No. 4,648,869 discloses a significant advance in the field of infiltration detection systems and methods. According to the Bobo patent, an infusion system infuses a test pulse of fluid to a patient. The test pulse creates a pressure wave response which can be monitor and used to detect if abnormal infusion has occurred.

Butterfield U.S. Pat. No. 4,710,163 discloses an infiltration detection system which uses the test pulse-pressure wave response concept of the Bobo patent. However, the Butterfield system compares the pressure wave response with a reference pressure wave response which represents the normal response when there is no infiltration. Specifically, the area between two curves representing these responses is used to attempt to detect infiltration. Thus, the Butterfield approach has the disadvantage of requiring that a normal pressure wave response be first determined and then stored for later comparison.

In other words, those infusion systems include a pressure transducer coupled to a microprocessor and suitable firmware or other programming that operate to monitor fluid pressure for purposes of detecting infiltration or other abnormal infusion condition. Such testing is sometimes called site checking or performing a site check and the Bobo and Butterfield systems perform the site check by infusing a test pulse of fluid to the patient, the test pulse creating a pressure wave response which can be monitored to detect infiltration or other abnormal infusion conditions.

The test pulse may be initiated in various ways, such as manually by depressing a pushbutton, or automatically under program control. In any case, the microprocessor examines the resulting pressure wave response and activates an abnormal-infusion-condition alarm if an abnormal infusion condition exists. The alarm serves to alert the attending medical staff that an abnormal infusion condition may exist so that corrective action may be taken before significant consequences develop.

It has been found that patient activity can induce artifacts in the pressure existing in the infusion system. These artifacts can be sufficient to create a false alarm condition or possibly to even mask a correct alarm condition. False alarms can mean wasted time and extra expense, effort, and patient involvement, as well as increased stress on responding personnel and adverse affects on morale, and so they represent a problem that needs to be overcome.

SUMMARY OF THE INVENTION

Recognizing that patient activity can significantly affect the pressure waveform including the pressure wave response and therefore alarm reliability, the present invention provides an infusion system that examines the pressure waveform for pressure artifacts characteristic of such activity. When any such artifacts are identified, the system forgoes performing a site check or indicates that the site check may be unreliable if already performed.

In other words, the system looks for pressure artifacts that may have been caused by patient activity. When the system detects the occurrence of such an artifact that exceeds a predefined level of departure from nominal system operation, it identifies it as patient-induced and sufficient cause to postpone, ignore, or rerun the site check.

Although the invention is particularly adapted for determining whether or not a site check should be made, more broadly it is applicable to detecting patient activity when a fluid is being infused into a patient. As such, the patient activity data can be used for various other purposes which may, or may not, be associated with site checks. For that broader purpose of the invention, the infusion system which incorporates the patient activity monitoring feature, may be pump-fed or gravity-fed.

Generally, an infusion system constructed according to a major aspect of the invention includes fluid-delivery means for delivering a fluid from a separate source of the fluid into a patient, transducer means for producing a signal related to the pressure of the fluid in the fluid-delivery means, and identification means responsive to the signal for identifying pressure artifacts characteristic of patient activity. According to the broader aspects of the invention, the fluid-delivery means may include a gravity-fed infusion arrangement or a flow control device such as a peristaltic pump. In addition, the identification means may include microprocessor circuitry and programming for examining the waveform of the signal under program control.

According to another aspect of the invention, the microprocessor means includes means for identifying pressure artifacts characteristic of patient activity amidst pressure changes caused by the fluid-delivery means. Then, the infusion system may perform a site check at a time of little patient activity for purposes of detecting an abnormal infusion condition. The system may be structured as subsequently described to provide a highly functional and significantly more reliable infusion system.

In line with the above, a method of detecting an abnormal infusion condition according to one aspect of the invention includes infusing a fluid into a patient through a conduit, with the pressure of the fluid in the conduit being subject to being influenced by certain patient activity. The method proceeds by monitoring the fluid pressure in the conduit in order to detect pressure artifacts characteristic of patient activity and performing a site check for abnormal infusion conditions at a time when no such pressure artifacts are detected. That may be done by as described above by producing a signal related to the pressure of the fluid in the delivery means and examining the waveform of the signal under program control.

Another way of ascertaining if patient activity is suitable for detecting abnormal infusion is to look for the occurrence of a baseline pressure during the normal delivery pattern which is unusually large in magnitude or which fluctuates excessively. That condition suggests that the pressure conditions in the conduit are not then suitable for detecting abnormal infusion, the fluctuating baseline conditions possibly being the result of a transient condition such as relatively slow movement by the patient. Thus, baseline fluctuations are useful only for detecting relative slow patient movement.

More specifically, the suitability of the pressure conditions in the conduit can be determined by comparing a function of the pressure of the fluid in the conduit during the normal delivery pattern to a threshold. That function of the pressure may be one or more pressure values or may be a function which is derived from one or more pressure values. In a preferred technique, the function of the pressure equals $B_1 + K(B_2)$ where $B_1$ is the baseline pressure at an instant prior to the test pulse, K is a constant, and $B_2$ is the rms value of a plurality of segments of the baseline pressure prior to the test pulse, and with at least one of the segments being prior to such instant.

Yet another method of detecting patient activity according to the invention is not necessarily concerned with infusion abnormalities. The method includes the steps of delivering fluid through a conduit into a patient, monitoring fluid pressure in the conduit, and identifying pressure artifacts characteristic of patient activity. Doing that enables a gravity-fed infusion system to double as a patient-activity monitor.

The foregoing and other objects and features of the invention and the manner of attaining them will become apparent and the invention itself will be best understood by reference to the following description taken in conjunction with the accompanying illustrative drawings.

BRIEF DESCRIPTION OF THE DRAWINGS

FIGS. 14-20 are flow charts of the PSA.

DESCRIPTION OF THE PREFERRED EMBODIMENTS

Figure 1:
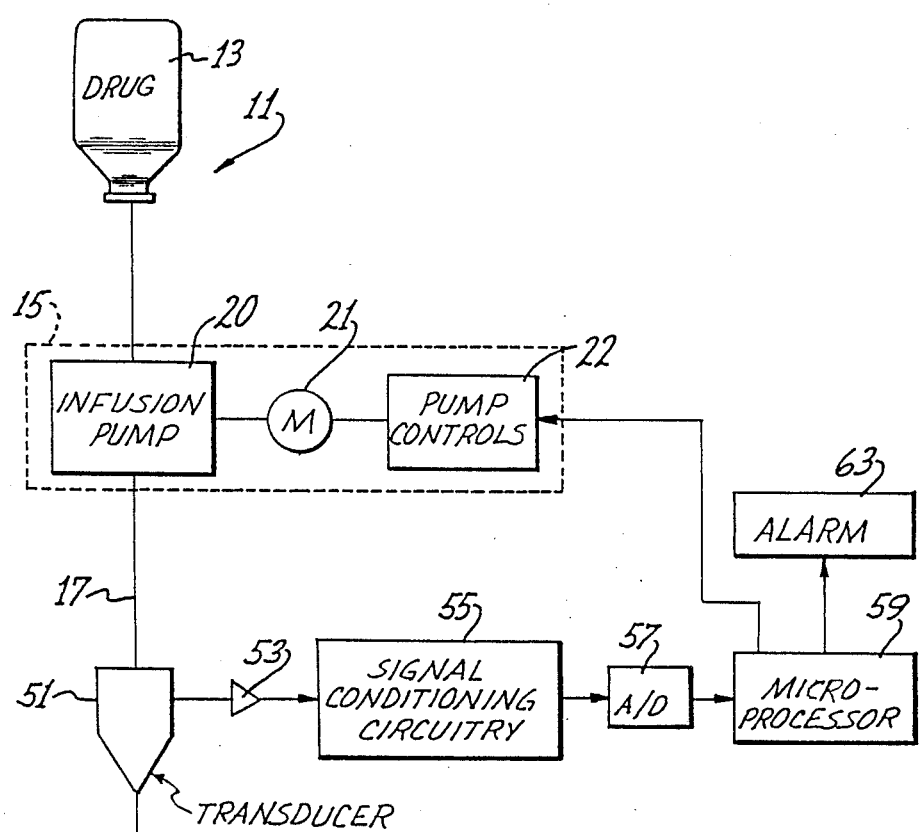
FIG. 1 is a block diagram illustrating one form of infusion system constructed in accordance with the teachings of the invention.

The description of the preferred embodiments is organized according to the following outline:
I. Infiltration Detection
II. Patient Activity Detection I. Infiltration Detection FIG. 1 shows an infusion system 11 which comprises a source 13 of a parenteral fluid, a flow control device or infusion device 15 for delivering the parenteral fluid through conduit means 17 to a patient. The conduit means 17 may comprise flexible tubing or other flow channels for supplying the parenteral fluid to the patient, and it combines with the infusion device 15 to serve as fluid-delivery means for delivering fluid from a separate source of the fluid (such as the source 13) into a patient.

The conduit means 17 terminates in a needle 18, such as an I.V. needle, which is adapted to be inserted into a vessel of the patient's vascular system so that the open distal end of the needle communicates with the interior of the vessel. In the illustrated embodiment, the needle 18 is inserted into a vein. If the open distal end of the needle communicates with tissue, as when the needle is forced completely through the vessel wall, infiltration has occurred.

The infusion device 15 may be any infusion device which is controllable to produce a test pulse 19 (FIG. 2) and, as such, may include an infusion pump, a controller, syringe, or the like. In the illustrated embodiment, the infusion device 15 includes a motor, such as a stepping motor 21, for driving the pump and pump controls 22 for controlling the motor. The pump 20 is a positive displacement pump, and accordingly, its output can be controlled by controlling the speed of the motor 21. The pump controls 22 control the motor speed as described more fully hereinbelow to provide the infusion device with the desired output.

Figure 2:
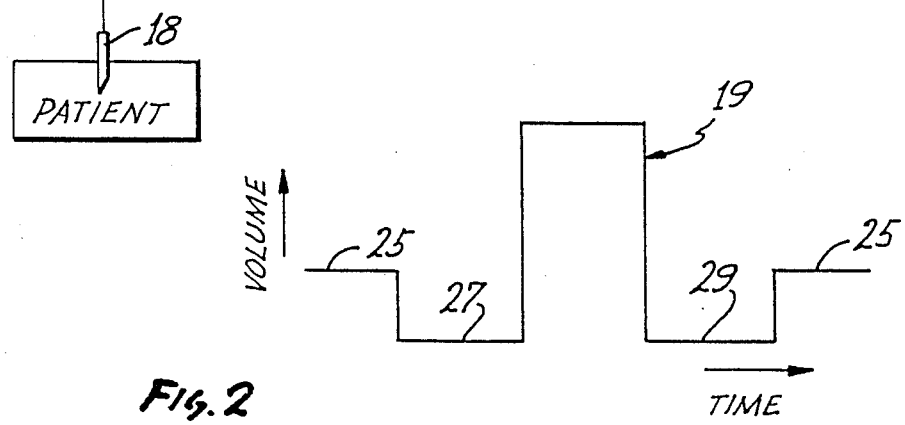
FIGS. 2-2E are plots of volume delivered by the infusion device versus time illustrating different examples of test pulses.

In a preferred construction, the infusion device 15 includes a peristaltic pump of the type disclosed in the U.S. Patent application Ser. No. 661,032 filed Oct. 15, 1984 entitled "Continuous Delivery Peristaltic Pump." That application is incorporated herein for the details of a peristaltic pump it provides. Such an infusion pump has a normal delivery pattern 25 which, in the present example, is essentially constant as shown by the flat portions of the pump delivery curve of FIG. 2. That is the result of accelerating through the deadband of the peristaltic pump. The curve of FIG. 2 is somewhat idealized in that the preferred infusion pump provides periodic short spikes and valleys of exceedingly short duration. However, those are sufficiently insignificant so that the normal delivery pattern of the pump can be considered as essentially constant, although a constant flow rate during the normal delivery pattern is not required.

The pump controls 22 periodically, and/or on demand, increase the speed of the stepping motor 21 to cause the infusion pump 20 to provide the test pulse 19 which, in the illustrated embodiment of FIG. 2, is in the form of an essentially square wave having a duration of approximately four seconds. As described more fully in Bobo Pat. No. 4,648,869, the infusion rate and hence the volume delivered during the test pulse preferably varies with the selected infusion rate for the infusion device 15. However, the duration of the test pulse 19 may be constant for all selected infusion rates. Selection of the infusion rate also results in selection of the associated flow rate for the test pulse 19. In that regard, the pump controls 22, as is common for infusion devices of this type, are programmable to enable the attendant to select or punch in a desired or selected infusion rate.

The pump controls 22 reduce the speed of the stepping motor 21 just before and just after each test pulse 19 to cause the infusion pump 20 to provide separating regions, which in the illustrated embodiment are leading and trailing infusion valleys 27 and 29, respectively, continuous to and on opposite sides of the test pulse 19. The valleys 27 and 29 are square waves of short duration during which the infusion rate is reduced sufficiently to wholly or partially compensate for the increased infusion rate which takes place during the test pulse 19. Preferably, the valleys 27 and 29 reduce the total flow by the same amount that the test pulse increases it so that the average or net effect across the valleys 27 and 29 and the test pulse 19 is an infusion rate equal to the rate represented by the normal delivery pattern 25. For example, each of the valleys 27 and 29 may have a duration which is twice as long as the duration of the test pulse 19, with such duration being eight seconds in the illustrated embodiment and constant for all selected infusion rates. The test pulse 19 and the valleys 27 and 29 constitute an altered pattern of flow.

Test pulses can be provided in various different ways, and additional examples of test pulses, which can be distinguished from the normal delivery pattern, are shown in FIGS. 2A-2E. Portions of the curves shown in FIGS. 2A-2E corresponding to portions of the curve shown in FIG. 2 are designated by corresponding reference numerals followed by the letter "a," "b," "c," "d," and "e," respectively.

Figure 2A:
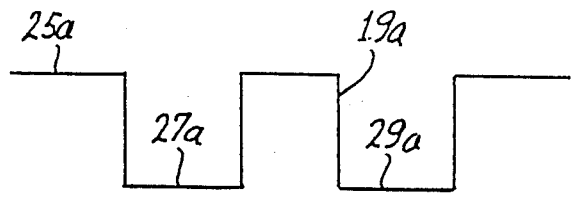

In FIG. 2A, the test pulse 19a is separated from the normal delivery pattern 25a by leading and trailing valleys 27a and 29a in much the same manner as disclosed in FIG. 2. However, the infusion rate during the test pulse 19a is the same as the infusion rate during the normal delivery pattern 25a. Although the infusion rates during the valleys 27a and 29a can be zero or negative, preferably, the infusion rates during those times are positive. Also, although the infusion rates during the valleys 27a and 29a can be different, they are, preferably, essentially the same.

Figure 2B:
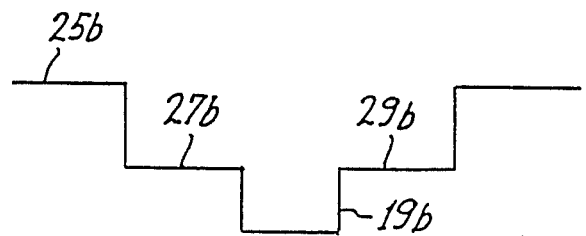

In FIG. 2B, the test pulse 19b is negative, i.e., the infusion pump 20 is reversed to create the infusion pulse. Although the infusion rate during the valleys 27b and 29b may be either positive or negative, in that embodiment, they are essentially zero.

Figure 2C:
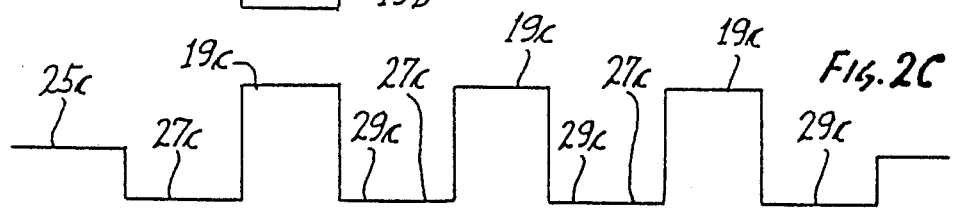

In FIG. 2C, a plurality of test pulses 19c is provided in relatively rapid succession before the infusion rate returns to the normal delivery pattern 25c. In that event, the valleys 27c and 29c between adjacent test pulses 19c constitute both trailing and leading valleys as shown.

Figure 2D:
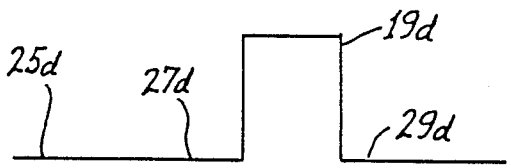

In FIG. 2D, the separating regions 27d and 29d are not distinguishable from the normal delivery pattern 25d, and so the altered pattern of delivery consists only of the test pulse 19d. That can be contrasted with the embodiments described above in which the altered pattern comprises both the leading and trailing separating regions and the test pulses.

Figure 2E:
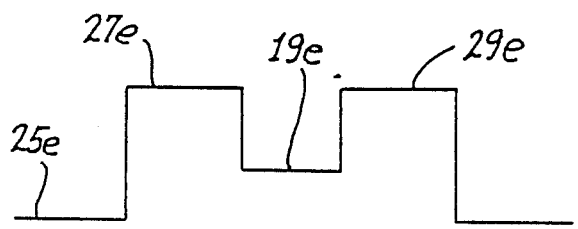

In FIG. 2E, the separating regions 27e and 29e represent periods during which the flow rate is greater than during the normal delivery pattern 25e, and the test pulse 19e represents a decreased flow rate which may be equal to, greater than or less than the flow rate during the normal delivery pattern. As illustrated, the flow rate during the test pulse 19e is greater than the flow rate during the normal delivery pattern 25e. Generally, test pulses of the type shown in FIGS. 2B and 2E, which have flow rates less than the adjacent separating regions, are not preferred.

Figure 3:
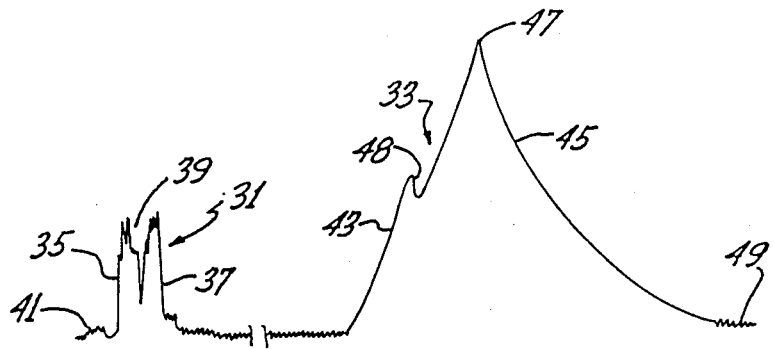
FIG. 3 is a plot showing one pressure wave response indicative of the fluid being properly supplied to the vessel of a patient and a second pressure wave response indicative of infiltration.

The presence of the test pulse 19 in the conduit means 17 creates a pressure wave response which has different characteristics depending upon whether or not the flowable material is being improperly supplied by the conduit means 17 to the patient. FIG. 3 shows examples of pressure wave responses 31 and 33 which indicate in-the-vessel and infiltration conditions, respectively. Although the pressure wave responses 31 and 33 are both shown in FIG. 3, they are not in scale in relation to each other. In reality, FIG. 3 shows curves which represent the pressure wave responses, but the curves, if desired, can be considered as the pressure wave responses.

The pressure provided by the pressure wave response 31 rises rapidly and almost instantaneously along a rising edge 35 and decays at about the same rate as represented by a falling edge 37. In between the edges 35 and 37, the pressure remains approximately constant, except for a short duration valley 39 which is repreesentative of the deadband of the peristaltic pump being employed. In that regard the pressure wave response 31 was generated by a peristaltic pump having a deadband and operating at about 350 cc's per hour, which is a high-delivery rate. If a peristaltic pump which accelerates through the deadband were employed, the duration and magnitude of the valley 39 would be greatly reduced. For this reason, it is preferred to utilize a peristaltic pump which does accelerate through the deadband so that any valley 39 would be of substantially less magnitude and duration than illustrated in FIG. 3. However, the pressure wave response 31 is essentially a square wave if the valley 39 is ignored. With the open distal end of the needle 18 of the conduit means 17 properly communicating with the interior of the vessel of the patient's cardiovascular system, the pressure wave response 31 is simply the result of forcing the additional fluid into the fluid carried by the vessel. For example, for an infusion rate of five cubic centimeters per hour (5 cc/hour), the pressure wave response 31 may rise about five millimeters of mercury (5 mmHg) above a baseline.

When infiltration occurs, the open distal end of the needle 18 is out of the interior of the vessel and communicates with tissue. As a result, the pressure wave response 33 is created in the conduit means 17. Specifically, the pressure wave response 33 rises along a rising edge or trailing portion 45 with both the rise time and fall time being much greater than for the pressure wave response 31. In addition, the pressure wave response 33 has a maximum pressure or peak value 47 which is much higher than the maximum pressure or peak value of the pressure wave response 31. For example, for an infusion rate of five cubic centimeters per hour (5 cc/hr), the pressure wave response 33 may rise about twenty millimeters of mercury (20 mmHg) above a baseline 49. The rising edge has a discontinuity 48 which is the result of using a peristaltic infusion pump to generate the pressure wave response 33 which did not accelerate through the deadband and, therefore, did not have an essentially constant delivery rate.

The pressure, or pressure response, of the parenteral fluid in the fluid-delivery means can be monitored in various different ways, such as by a pressure transducer 51 which provides an electronic analog pressure signal related to the pressure in the conduit means 17, the transducer 51 serving as transducer means for producing a signal related to the pressure of the fluid in the delivery means. In the illustrated embodiment, the pressure signal from the transducer 51 is amplified by an amplifier 53, conditioned in signal conditioning circuitry 55 and sampled in an analog-to-digital converter (i.e., A/D converter 57) which provides the samples to a microprocessor 59. The signal conditioning circuitry 55 is conventional and is provided for the purpose of adusting or compensating for various variables, such as temperature. Of course, if those variables are not considered significant, the signal conditioning circuitry 55 can be eliminated.

The samples of the pressure signal from the transducer 51 may be taken continuously or taken only during the sample time. In the former case, the microprocessor 59 is used to separate the samples taken during the sample time from those which are not. However, in the illustrated embodiment, the A/D converter 57 samples the pressure signal continuously and provides the samples in a digital format to the microprocessor 59.

The sampling frequency of the A/D converter 57 is preferably higher than the sampling frequency required for detecting infiltration or other abnormal infusion. For example, if infiltration detection requires about one sample per second, samples may be taken at, for example, five samples per second, forty samples per second, etc. The samples can then be combined in any of a variety of ways to produce an overall sample value for each second by the microprocessor 59. In any event, the microprocessor 59 performs an integration function as described below to determine if infiltration has occurred.

Figure 4:
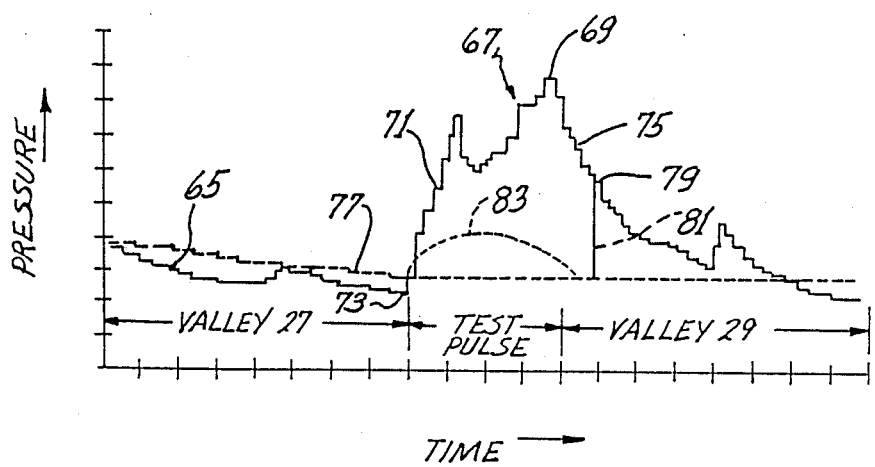
FIG. 4 is a plot showing the relationship of the pressure response to the infusion rate for infiltration conditions and normal conditions.

FIG. 4 shows a pressure response 65 in the conduit 17 as measured by the transducer 51 in response to infusion of fluid through &:he conduit to the patient. As shown, the pressure generally diminishes during the valley 27 until the leading edge of test pulse 19, at which time a pressure wave response 67 is initiated. The response 67 is indicative of abnormal infusion (e.g., infiltration). The pressure wave response 67 rises, with modest interruption to a peak value 69 of pressure which is reached at approximately the end of the test pulse 19. The pressure then slowly decays during the valley 29, again with modest interruption, to the end of the valley 29. Thus, the pressure wave response 67 has a leading portion 71 that extends from an initial point 73 at the beginning of the test pulse 19 to the peak value 69 and a trailing portion 75 that extends from the peak value 69 to a baseline 77.

The baseline 77 can be established by the microprocessor 59 in various different ways and is preferably a function of the pressure response 65 intermediate test pulses 19. More specifically, the baseline 77 can be established by suitably smoothing the pressure response 65 between test pulses 19, and this function can be carried out by the microprocessor. Accordingly, the baseline 77 lags the pressure response 65. However, at the initiation of the test pulse 19, the baseline 77 then existing is frozen by the microprocessor such that it remains essentially constant throughout at least the test pulse 19 and the trailing valley 29.

Various different techniques can be used to smooth the pressure response 65 between test pulses 19. According to one preferred smoothing technique, the pressure samples from the A/D converter 57 are slew-rate limited and averaged to provide pressure values for updating the baseline 77. By way of illustration and not by way of limitation, the A/D converter 57 may provide forty pressure samples per second, and the slew-rate limiting processing limits each sample to a value which is no greater than 1.25 times, and no less than 0.75 times, the value of the previous sample. Following that, a one-fourth second average of ten of the samples is taken, and that average value provides a new point for updating the baseline 77. With that technique, four new smoothed pressure readings are provided each second. The baseline 77 is then typically derived by passing those samples through an additional smoothing process, such as a single-pole, low-pass filter with a time constant of about two seconds.

A primary advantage of slew-rate limiting is that it can eliminate spurious spikes that may occur in the pressure response 65 that might be incorrectly interpreted as the peak value 69. In addition, slew-rate limiting and averaging provides a desired smoothing effect for the baseline 77 to reduce transient irregularities that might otherwise occur in the baseline 77.

To determine if infiltration or other abnormal infusion has occurred, the area between the pressure wave response 67 and the baseline 77 is calculated by the microprocessor between the initial point 73 and a truncation point 79. In the illustrated embodiment, the truncation point 79 is the tine at which the pressure on the trailing portion 75 drops to fifty percent of the peak value 69. More generally, the truncation point 79 is the first to occur of a pre-established percent of the peak value 69 and the end of the trailing valley 29. Because the predetermined percent of the peak value 69 occurred first in the example of FIG. 4, the integration is truncated at this point along a line 81.

Alternatively, or in addition thereto, the integration of the pressure wave response 67 may proceed from the initial point 73 to the peak value 69 to provide a front end area. This front end area may be used in lieu of, or in addition to, the truncated area (i.e., the area obtained from integrating from the initial point 73 to the truncation point 79) to determine whether or not infiltration has occurred.

FIG. 4 also shows a somewhat idealized pressure wave response 83 in dashed lines which is indicative of the proper supply of fluid to the patient. The pressure wave responses 67 and 83 would, of course, not exist simultaneously, but they are shown together for comparative purposes. Applying the same criteria for integration of the pressure wave response 83, virtually the entire area between the pressure wave response 83 and the baseline 77 would be determined. However, that area is much less than the area obtained by the truncated integration of the pressure wave response 67. Accordingly, the microprocessor 59 can readily determine whether or not infiltration has occurred.

The area information can be used in various different ways to arrive at a decision regarding the presence or absence of infiltration or other abnormal infusion conditions. For example, both the truncated area and the front end area may be normalized and compared with known thresholds, and an alarm condition may be declared in response to one or more of those areas exceeding the established threshold. In a preferred decision-making technique, an alarm condition is not declared until three consecutive normalized truncated areas or three consecutive normalized front end areas resulting from three consecutive test pulses have exceeded their respective thresholds. More specifically, in one technique, the truncated area is normalized by dividing it by a divisor which is a function of the difference between the infusion rate during the test pulse and the infusion rate during either of the valleys 27 and 29. Preferably the function is simply the difference between these infusion rates. The quotient or normalized area is then compared with a known threshold. The front end area is normalized in the same way and compared with its threshold.

Thresholds will vary with the fluid circuit (i.e., the fluid delivery means) depending upon such things as tubing diameter and length, cannula size, the presence of filters, and the like. Therefore, needle size is not always the most important factor. Regarding the gauge or size of the needle, however, the areas can be effectively normalized for the size of the needle 18 or other cannula by employing different thresholds for different ranges of needle size. Examples of suitable thresholds for both truncated area and front end area as a function of needle gauge are shown in the following Table A.

TABLE A

| Needle Gauge | Thresholds | |
|---|---|---|
| | Front-End Area | Truncated Area |
| 16–18 | 0.1 | 0.2 |
| 19–21 | 0.3 | 0.6 |
| 22 and above | 0.5 | 1.0 |

Thus, if a sixteen gauge needle is used with a nominal fluid circuit, an alarm condition indicative of abnormal infusion would be declared if any three consecutive test pulses yielded a normalized truncated area of greater than 0.2 or a normalized front end area of greater than 0.1.

In Table A it is assumed that the units on the area of pressure wave response are mmHg-seconds and that the infusion rates are in milliliters per hour. Of course, different units can be employed, and the thresholds adjusted accordingly.

Another feature of the invention is to ascertain if pressure conditions in the corduit means 17 are suitable for detecting if fluid is being improperly supplied by the conduit means to the patient. Although that feature of the invention may be particularly adapted for use with the integration technique of the invention, its use is not so limited, and it can be used with other techniques for determining whether or not abnormal infusion exists.

The suitability of the pressure conditions in the conduit means 17 can be evaluated in various different ways to determine if those conditions are suitable for detecting abnormal infusion. That can be accomplished, for example, by comparing a function of the pressure of the fluid in the conduit means 17 during the normal delivery pattern 25 to a threshold. Although the function of the pressure of the fluid in the conduit means 17 can be the raw pressure samples from the A/D converter 57 per se, preferably that function includes some form of smoothing.

According to a preferred technique, the following equation is used:

$$BQI = B_l + K(B_2)$$

where BQI is a baseline quality index, $B_l$ is the magnitude of the baseline 77 prior to the valley 27, K is a constant (which may be the value three, for example), $B_2$ is the rms value of a plurality (such as one hundred twenty) of baseline 77 magnitudes occurring just prior to the baseline magnitude representing $B_l$.

Thus, BQI is a function of the pressure in the conduit means 17. Assuming that the pressure response 65 is slew-rate limited, averaged, and low-pass filtered to determine the baseline 77 as described above, then $B_l$ is the last baseline 77 value prior to the valley 27, and $B_2$ is the rms value of 120 baseline values immediately preceding the value used for determining $B_l$.

It has been found that if BQI (as calculated using the equation set forth above) exceeds a threshold, the pressure conditions in the conduit means 17 are not suitable for determining whether or not abnormal infusion exists. Although that threshold can be adjusted as desired, by way of example, a threshold of eighty-five millimeters of mercury (85 mmHg) is suitable for many applications.

Figure 5B:
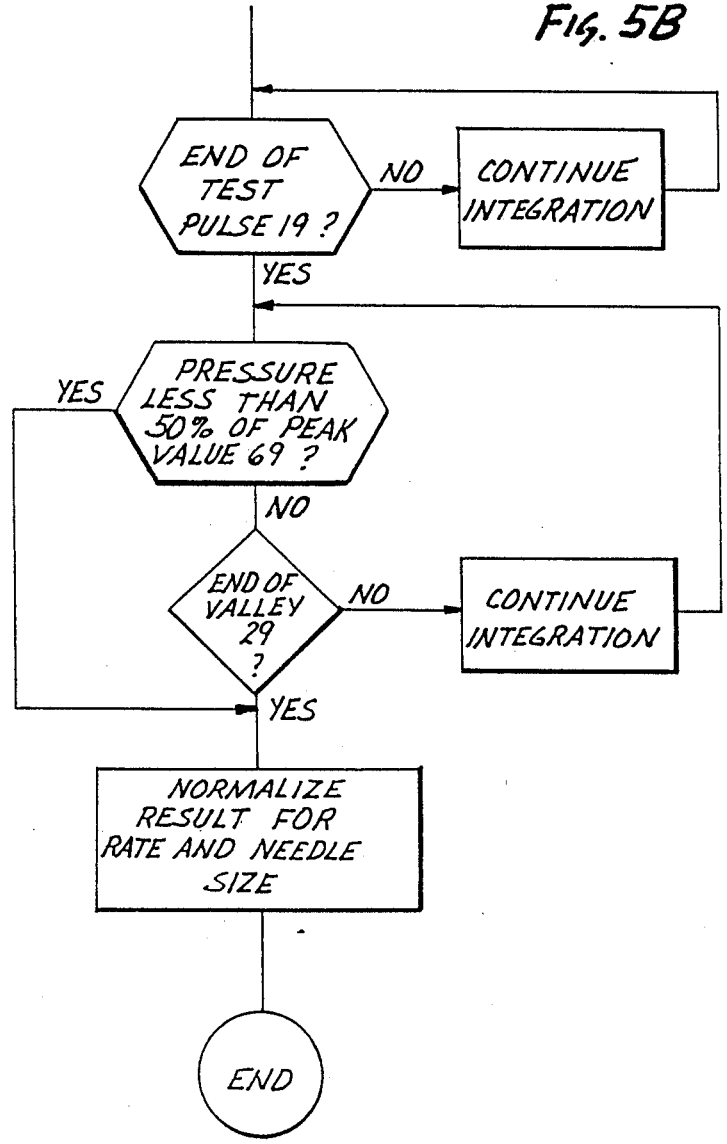
FIG. 5 (the combination of FIG. 5a and FIG. 5b) is a flow chart showing how the system functions to detect infiltration.

FIG. 5 is a flow chart showing the basic steps in the truncated integration process of the invention. As shown in FIG. 5, when the end of the valley 29 occurs, a new BQI calculation commences using the BQI equation set forth above. When the time for the next site check (i.e., the time to initiate the altered infusion pattern represented by the valley 27, the test pulse 19, and the valley 29 occurs, it is allowed to proceed only if the BQI is below the threshold magnitude as described above. In that regard, the next site check referred to in FIG. 5 may be manually initiated by entering information into the infusion device 15 or in response to programming of the infusion device 15 to provide site checks at specified times or at specified intervals. In any event, the infusion device 15, and in particular, the infusion pump 20 will provide the reduced infusion represented by the valley 27 only if the BQI is below the specified threshold.

When the end of the valley 27 is detected (i.e., the start of the test pulse 19) the baseline 77 is frozen and integration of the difference between the baseline and the pressure wave response commences as shown in FIG. 5. The integration continues from the initial point 73 beyond the end of the test pulse 19 until the first to occur of a pressure less than fifty percent of the peak value 69 or the end of the trailing valley 29. At the end of the integration, the truncated area and the front end areas are normalized for infusion rate and needle-size effects as described above.

Following that, the microprocessor 59 makes a decision concerning abnormal infusion as described above, and if infusion is abnormal, the alarm 63 is energized and/or infusion is terminated. Of course, the microprocessor may require information from multiple site checks before declaring abnormal infusion.

The abnormal infusion may be the result of any condition, such as infiltration, occlusion of the conduit means 17, clotting or phlebitis, which leads to the creation of the pressure wave response 67 (FIG. 4). In any event, once the abnormal infusion is declared, an attendant can determine the particular cause and seek to remedy it.

II. Patient Activity Detection

Generally, with regard to patient activity detection, the invention includes fluid-delivery means for delivering a fluid from a separate source of the fluid into a patient and transducer means for producing a signal related to the pressure of the fluid in the fluid-delivery means. The fluid-delivery means function is accomplished in the infusion system 11 (FIG. 1) by the combination of the infusion device 15 and the conduit means 17, the source 13 constituting the separate source of fluid and the transducer 51 functioning as the transducer means.

Although the infusion system 11 includes an infusion device, the fluid delivery means need not necessarily include an infusion device within the broader inventive concepts disclosed. In other words, the fluid-delivery means may take the form of a gravity-fed infusion arrangement in which the source 13 is elevated relative to the needle 18, and the infusion system 11 is intended to serve as a illustration of such a gravity-fed system. In that case, the infusion device 15 is to be considered omitted from the infusion system 11.

According to a major aspect of the invention, the system includes identification means responsive to the signal for identifying pressure artifacts characteristic of patient activity. That function is accomplished in the system 11 by the microprocessor 59 which is, preferably, supported by the amplifier 53, signal conditioning circuitry 55, A/D converter 57, and alarm 63 as described in detail with regard to the infiltration detection aspects of the illustrated embodiment. In other words, the identification means includes microprocessor means for examining the waveform of the signal under program control, and the microprocessor means includes means for identifying pressure artifacts characteristic of patient activity, that being done with the programming subsequently described.

Details of the programming employed for patient-activity detection are subsequently described with reference to the waveforms illustrated in FIGS. 6-13 and the flow charts in FIGS. 14-20. As mentioned previously, in order to increase the probability that infiltration detection is reliable, it is necessary to have a mechanism for determining when patent-induced pressure noise is at a minimum, or at least within tolerable limits. Patient-induced pressure noise can cause both extremely high and low TPI values, which could result in a false infiltration alarm, missed infiltrations, false pump height alarms, or other false meanings given the TPI calculations.

Patient-activity detection is accomplished with programming that can be referred to as a pressure stability algorithm (PSA). The PSA makes determinations based on the pressure waveforms as to when it is best to schedule or perform a site check. It does not guarantee the absence of patient noise during the site check, only that the probability of getting patient-induced noise during the site check is very low. As discussed earlier, infiltration detection itself may include algorithms for determining if the site check was corrupted by patient noise during the site check.

It is desirable in the context of infiltration detection to know when the pressure waveform read by the system is being affected by external noise events, such as patient activity. Some existing infiltration detection approaches (such as Butterfield Pat. No. 4,743,228) mention requirements of "sedentary patients" as a prerequisite to infiltration detection. But the present invention includes a method for identifying random noise in the pressure signal caused by some external event other than the infusion device. Specifically, it is used in the context of infiltration detection to determine optimal times to schedule site checks. Preferably, it includes a system having a flow control device, pressure transducer, micro-processor, and suitable firmware for determining the presence of non-pump noise (i.e., patient induced) in the pressure waveform read by the system.

Clinically, most patients have periods of activity during which it is undesirable to check the IV site for infiltration because the pressure waveform is primarily being influenced by the patient activity. However, it is noted that in even the most active patients, it is usual for there to be several minutes between the periods of extreme activity during which there is no patient-induced noise (no patient-induced artifacts) in the pressure waveform. The present invention allows the system to take advantage of such quiet periods to run the infiltration detection technology.

The PSA is based on the observation that linear peristaltic pumps create a unique and well defined, periodic, pressure waveform when delivering fluid. In other words, they cause pressure changes that can be recognized as having been induced by the pump. Correspondingly, noise in the pressure waveform generated by an external agent, such as that induced by patient activity, is random, larger in amplitude, and non-uniform. They are referred to herein as patient-induced artifacts (i.e., artifacts characteristic of patient activity).

In a general sense, many pattern recognition techniques could be employed to discern between periodic, non-random, pressure waveforms and random, non-uniform pressure waveforms. However, in the context of an infusion device, the nominal pressure response generated by the infusion device is unique, periodic, and predictable and it contains specific features, some more easily identified than others.

Figure 6:
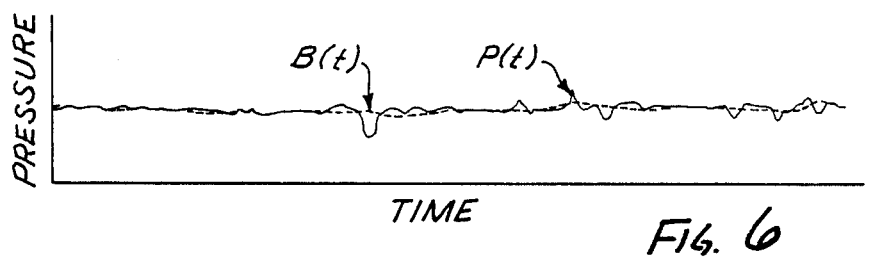
FIGS. 6-13 are plots of various pressure waveforms illustrating pump noise at lower infusion rates (system-induced pressure changes), pump noise at higher infusion rates, patient noise (patient-induced artifacts in the pressure waveform) amidst the pump noise, and various techniques used in identifying patient-induced artifacts.
Figure 7:
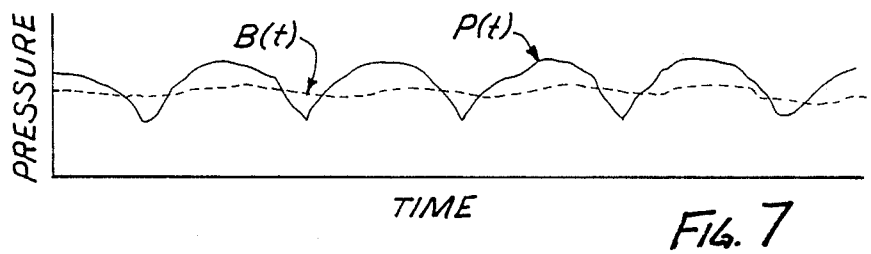
Figure 8:
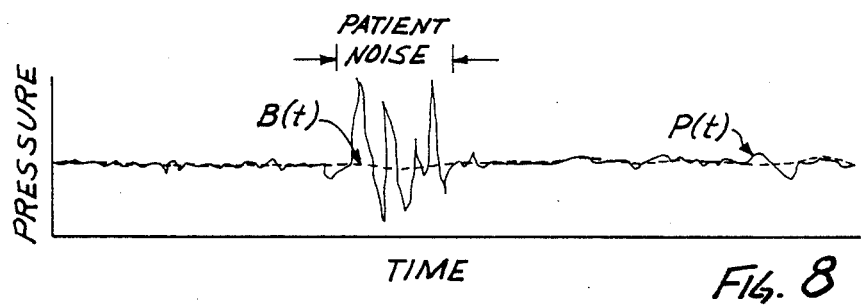
Figure 9:
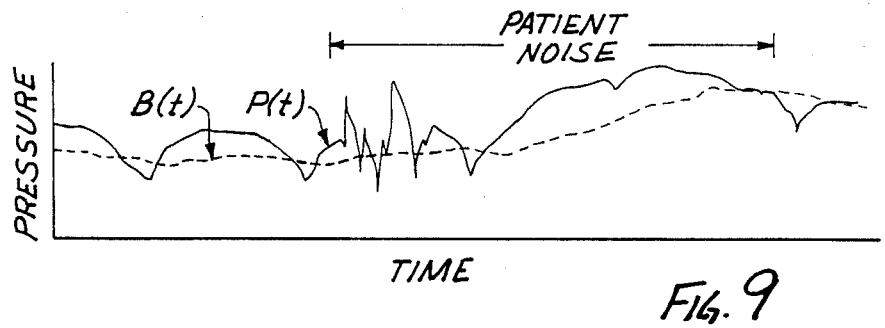
Figure 10:
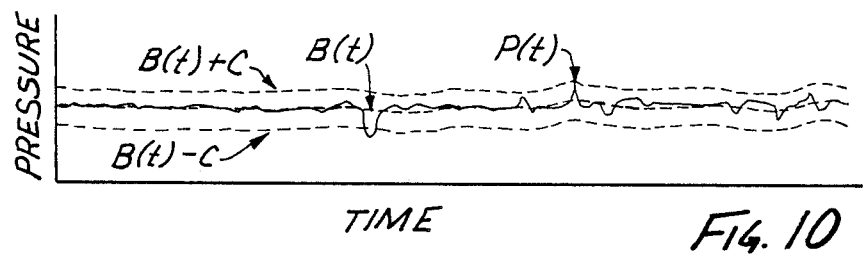
Figure 11:
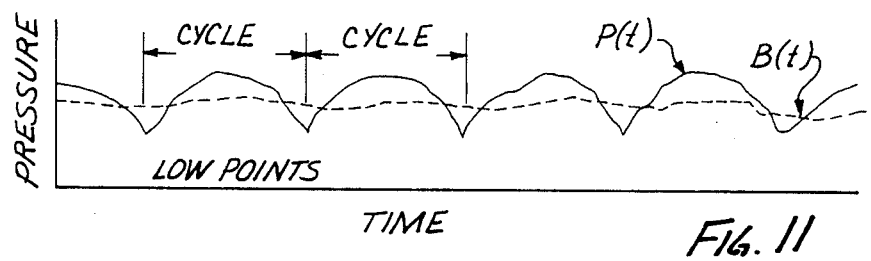
Figure 12:
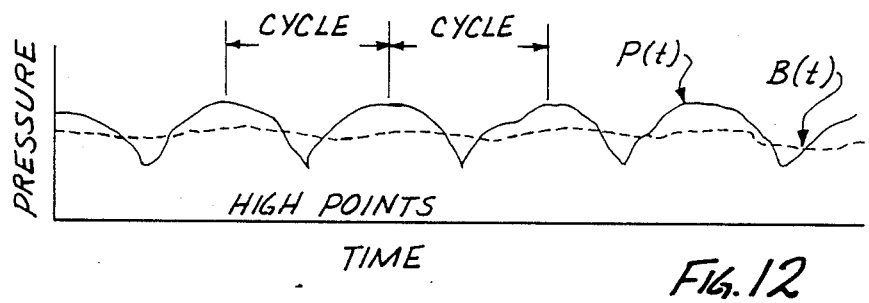
Figure 13:
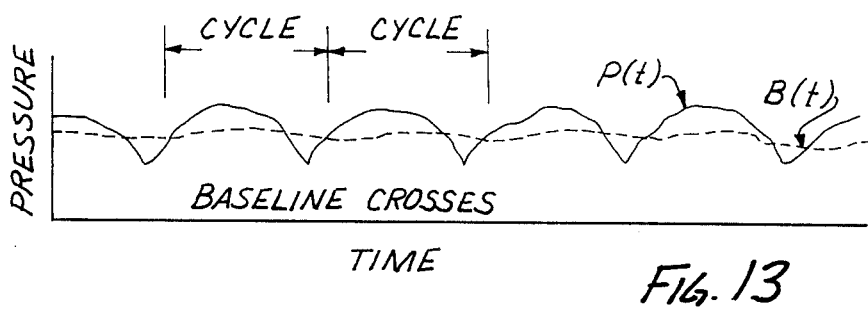

Each time the pump goes through deadband, the pressure in the conduit drops off sharply. After deadband has completed, the pressure increases continually until the next deadband occurs. That cyclic behavior creates a pressure graph that looks similar to a sine wave. For very low rates such as 0–50 cc/hour, the wave is long and flat as illustrated in FIG. 6, and for high rates (generally greater than 200 cc/hour) the amplitudes are large and the period very small as illustrated in FIG. 7. Also, as the rate increases, the stability of the wave increases. The PSA is based on that behavior.

A pressure waveform generated by a linear peristaltic infusion device while running at lower infusion rates appears as a straight line pressure plot with some low-amplitude hash superimposed corresponding to the rate at which the infusion device motor is advanced. In that case, the PSA searches the pressure waveform for pressure deviations exceeding a pair of thresholds some number of times, the explanation for substantial changes in pressure being patient activity or other external pressure-affecting events.

Specifically, when the infusion pump is running at lower rates, the pumping action a low-amplitude, hashed, pressure waveform similar to the hashed pressure waveform illustrated in FIG. 6. At higher rates, the pump causes periodic sinusoidal pressure changes (a periodic sinusoidal pressure waveform) with a specific period corresponding to the time required to complete a pump cycle. It is similar to that illustrated in FIG. 7.

During a pump cycle, several repeating waveform characteristics are evident, such as pressure low points, pressure high points (dp/dt=0), pressure/baseline crosses, etc. The frequency of a repeating waveform feature (e.g., pressure low point) is used to confirm the presence of nominal system-induced pressure changes. However, should it become impossible to measure a consistent interval between successive repeating features, or if the interval changes significantly (e.g., ±10%), the PSA declares the pressure environment too noisy for site checks. Patient noise, on the other hand, produces random changes in pressure, similar to that shown in FIGS. 8 and 9.

FIGS. 10–13 illustrate periodic characteristics use by the PSA in identifying patient-induced artifacts. The baseline or B(t) is computed by the PSA using the formula:

$$B(t) = (15/16)B(t-1) + (1/16)P(t)$$

where B(t) is the new baseline value, B(t−1) is the old baseline value at an instant prior to the computation, and P(t) is the pressure. The PSA takes both forms of pressure changes into account in the process of identifying patient-induced pressure artifacts, pressure artifacts characteristic of patient activity being shown in FIG. 8 amidst the pressure changes caused by the fluid-delivery means that are illustrated in FIG. 6, and in FIG. 9 amidst the pressure changes caused by the fluid-delivery means that are illustrated in FIG. 7.

Figure 14:
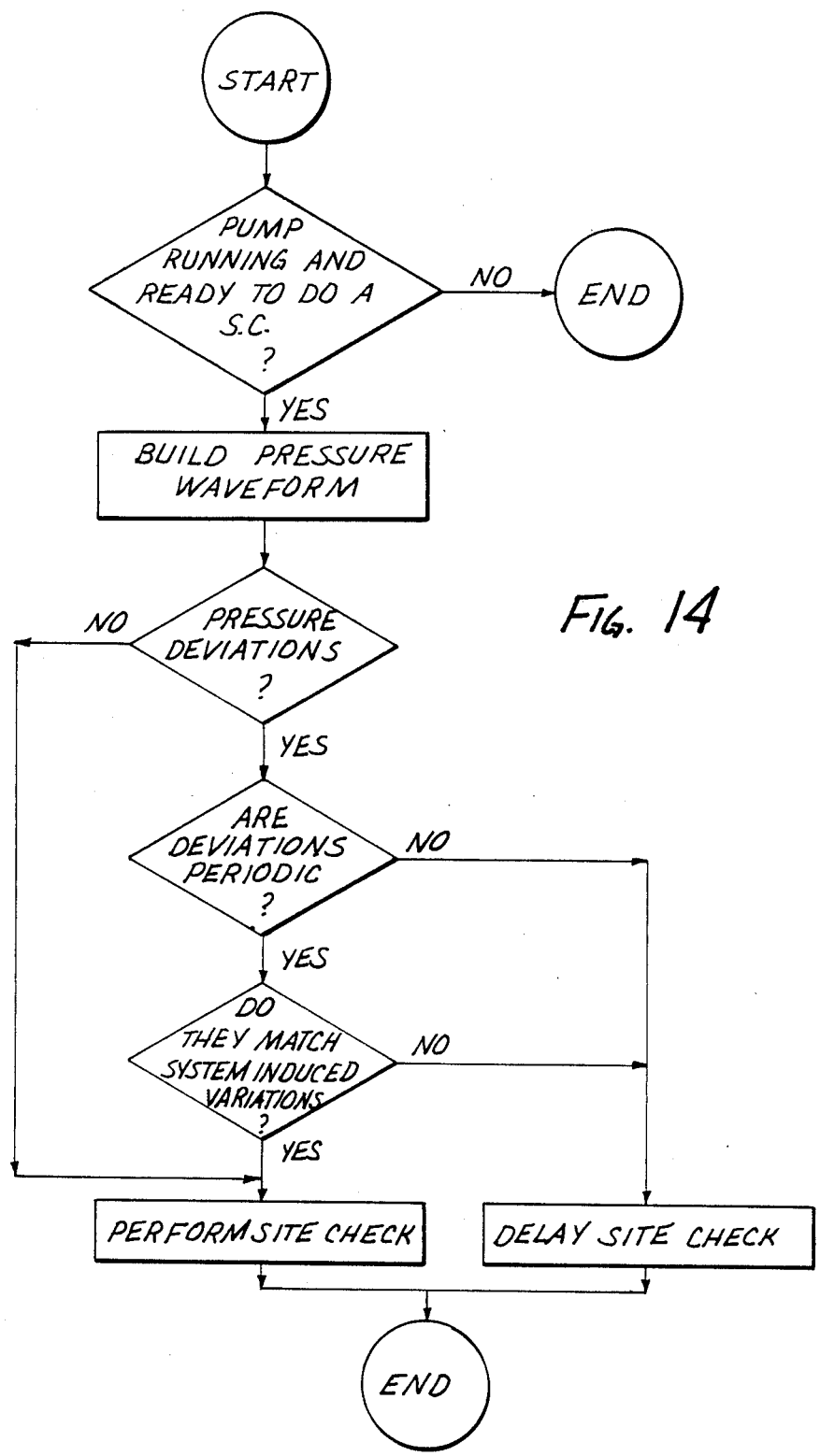

Although other programming can be used within the broader inventive concepts disclosed, the illustrated embodiment utilizes the PSA for which a top level flow chart is provided in FIG. 14. The PSA only becomes activated when the system 11 is operative for performing site checks. The input to the PSA consists of a pressure waveform that is plotted over a given interval of time. It is characterized by pressure points which are derived from the absolute pressure in the conduit means, and a baseline which is a function of P(t). Once the pressure waveform is built, the PSA can perform an analysis on the resulting pressure curve to determine if the curve is a result of system-induced noise, patient-induced noise, or both.

The baseline tracks the pressure responses in a slow fashion, so that it acts as a smoothed version of the actual pressure curve. If the baseline and the pressure response are essentially the same line, then it is assumed that no patient noise is present in the pressure waveform. However, if the pressure deviates from the baseline by a predetermined constant amount, a predetermined number of times, then it is necessary to continue processing the waveform in order to determine if the pressure deviations are a result of the system or patient artifacts.

System-induced noise is very predictable and periodic. One can use many criteria to determine if the pressure is periodic such as looking for large amplitude pressure, small amplitude pressure, low points, places where the pressure crosses the baseline, and even changes in slope (dp/dt). Whatever the criteria, it is necessary to determine if one, all, or any combination of the above criteria occur at predictable intervals in time.

For example, consider the use of low points to establish periodic behavior By knowing the rate of infusion, it is easy to calculate what the distance between each low point should be, so in finding just one low point, all other low points can be predicted. By using the low points the pressure graph can be divided into cycles as in FIG. 11. When the number of times that the pressure crosses the baseline in one cycle exceeds some predetermined constant, the waveform is declared to be non-periodic due to the presence of unpredictable low points between the two reference low points.

Even when the waveform has been declared periodic, patient noise might be present. It must be established that the periodic units in the pressure waveform are consistent with system-induced variations. System-induced variations are consistent, and therefore the shape and size of the periodic units should be consistent plus or minus some predetermined tolerance. For example, comparing the difference in average amplitudes between all contiguous periodic units to some predetermined threshold will indicate whether there is patient noise or not.

FIG. 15 provides an expansion of the "build pressure waveform" operation shown in FIG. 14. The pressure collected from the system is plotted on a two dimensional graph, with the X axis being in units of time and the Y axis being in mmHg of pressure. Adding a new pressure reading, P(t) to the graph consists of putting a point at the (x,y) coordinate where x=t and y=pressure in mmHg, then drawing a line between the previous point and the new point.

The baseline B(t) represents a smoothed version of P(t). B(t) is only allowed to move in the Y direction by 1/16 of P(t).

Adding a new baseline reading, B(t) to the graph consists of putting a point at the (x,y) coordinate where x=t and y=baseline pressure in mmHg, then drawing a line between the previous point and the new point.

It is necessary to determine when enough data points have been collected in order that the PSA can make an accurate determination about &:he pressure waveform. Since the PSA is looking for periodic pressure behavior, and those periods have a one-to-one correspondence to pump motor revolutions, it is necessary for the algorithm to collect data across a time period of at least two motor revolutions.

For example, a requirement of the system 11 may be for the time axis on the pressure waveform to be greater than or equal to fifteen seconds, and less than or equal to sixty seconds. If an integer number of pump motor revolutions cannot be fit into a time axis of sixty seconds, then a fifteen-second time interval is used, making the assumption that for cases where the periodic pressure interval of the system is greater than thirty seconds, the system noise will be insignificant when compared to any patient induced noise. Simplified, the word "Complete" in the flow chart in FIG. 15 takes on the following meaning:

| Complete = | a. | >= 2 revolutions have occurred in a time interval of fifteen to sixty seconds; or |
|---|---|---|
| | b. | if condition "a" cannot be met, then fifteen seconds. |

FIG. 16 provides an expansion of the "pressure deviations" operation shown in FIG. 14. The statement "For t=1 to n" dictates that all of the statements between that one and the statement "End for loop" will be executed exactly (n−1) times. The first time the encapsulated statements are executed, "t" will equal 1, the second time "t" will equal 2, etc., until the last time through when "t" will equal "n."

According to one aspect of the invention, the microprocessor means is responsive to the amplitude of the signal exceeding a predefined threshold. In that regard, the PSA must determine if significant pressure deviations (P(t)) have occurred in the pressure curve. It does that by comparing the absolute value of B(t) −P(t) for all points on the curve to some fixed threshold. A count is maintained of the number of times that the difference is greater than the threshold (such as 7 mmHg, for example).

A single count of (B(t) −P(t))>threshold does not necessarily indicate that there is a significant amount of noise in the system. The counter must exceed some threshold amount of counts (which can be determined empirically for each system and will vary with such variables as rate) before excessive pressure deviations are declared by the PSA. For example, the threshold counts used in the system 11 are base on the following Table B.

TABLE B

| Rate | Counts threshold |
|---|---|
| 16 to 21 | 16 |
| 22 to 31 | 12 |
| 32 to 62 | 8 |

TABLE B-continued

| Rate | Counts threshold |
|---|---|
| others | 4 |

According to another aspect of the invention, the microprocessor means is responsive to the waveform of the signal having a periodic pattern characteristic of the fluid-delivery means. In that regard, FIG. 17 provides an expansion of the "are deviations periodic" operation shown in FIG. 14. Generally, identifying repeating features in the waveform (i.e., low points, high points, dp/dt=0, baseline crosses) and then evaluating the interval between repeating features can be used to determine that the pressure waveform only contains system-induced pressure changes. It may be said in that regard that the microprocessor means includes means for identifying pressure artifacts characteristic of patient activity amidst pressure changes caused by the fluid-delivery means. External noise, such as patient-induced noise, will affect the pressure waveform in a random fashion. Therefore, the occurrence of repeating features will be random, with no discernible interval.

The pressure waveform can only be divided into periodic units (cycles) if the pressure waveform contains repeating patterns (i.e., periodic). If the pressure is not periodic (i.e., it is random), then the PSA will delay the site check. To save processing time, it is very useful to assume where the low points in the curve should occur. For example, in the system 11 the PSA knows when the low points should occur based on the position of rotation of the pump motor.

According to another aspect of the invention, the microprocessor means is responsive to the number of zero crossings of the signal exceeding a predefined number. By assuming where the periodic: points of negative amplitude (P(t)−B(t)<0) occur, the pressure points between the two assumed lows should not be minimums (P(t)−B(t)<0). A count is maintained for each cycle of the number of times that the pressure curve crosses the baseline curve. If the count is high for any of the units, then unpredictable minimums are occurring between the assumed low points, and it can be concluded that the pressure behavior is non-periodic.

Figure 18:
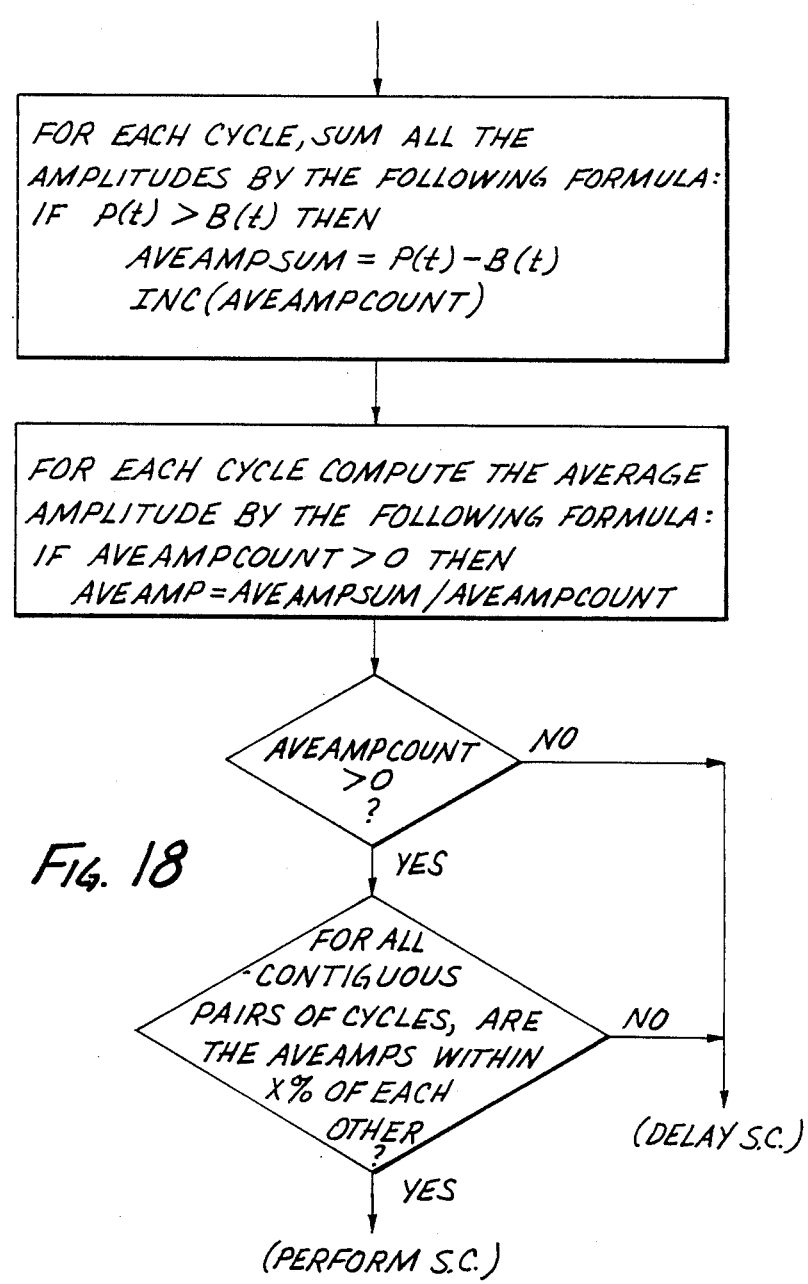

FIG. 18 provides an expansion of the "do they match system induced variations" operation shown in FIG. 14. System-induced variations are very consistent, whereas patient-induced variations tend to be random. The size and shape of each cycle should be about the same if only system noise is present. A good measurement of size and shape is average amplitude and according to another aspect of the invention, the microprocessor means is responsive to the waveform of the signal having an average amplitude exceeding a predefined value. To compute average amplitude, all of the positive amplitudes (P(t) −B(t)) are summed for a given cycle, then divided by the number of items summed.

System-induced noise dictates that there will be positive deflections of pressure (P(t)>B(t)) during one cycle. If no positive amplitudes are found, then the site check is delayed.

According to another aspect of the invention, the microprocessor means is responsive to the waveform of the signal having a repeating pattern occurring at regular intervals. Since system-induced noise is consistent, all consecutive cycles should have about the same shape and size. If any of the average amplitudes of consecutive cycles differ by a fixed percent, then the site check will be delayed.

FIG. 19 provides an expansion of the "perform site check" operation shown in FIG. 14, and FIG. 20 provides an expansion of the "delay site check" operation. Those expansion are self explanatory.

In line with the above, a method of detecting an abnormal infusion condition according to one aspect of the invention includes infusing a fluid into a patient through a conduit, with the pressure of the fluid in the conduit being subject to being influenced by certain patient activity. The method proceeds by monitoring the fluid pressure in the conduit in order to detect pressure artifacts characteristic of patient activity and performing a site check for abnormal infusion conditions at a time when no such pressure artifacts are detected. That may be done by as described above by producing a signal related to the pressure of the fluid in the delivery means and examining the waveform of the signal under program control.

Another method of detecting patient activity according to the invention is not necessarily concerned with infusion abnormalities. The method includes the steps of delivering fluid through a conduit into a patient, monitoring fluid pressure in the conduit, and identifying pressure artifacts characteristic of patient activity. Doing that enables a gravity-fed infusion system to double as a patient-activity monitor.

Thus, recognizing that patient activity can significantly affect the pressure waveform including the pressure wave response and therefore alarm reliability, the present invention provides an infusion system that examines the pressure waveform for pressure artifacts characteristic of such activity. The system looks for pressure artifacts that may have been caused by patient activity, and when it detects the occurrence of such an artifact that exceeds a predefined level of departure from nominal system operation, it identifies it as patient-induced and sufficient cause to postpone, ignore or rerun the site check.

Although an exemplary embodiment of the invention has been shown and described, many changes, modifications, and substitutions may be made by one having ordinary skill in the art without necessarily departing from the spirit and scope of the invention.

What is claimed is:

1. An infusion system, comprising:
    fluid-delivery means for delivering a fluid from a separate source of the fluid into a patient;
    transducer means for producing a signal related to the pressure of the fluid in the fluid-delivery means;
    identification means responsive to the signal for ascertaining if the level of patient activity is suitable for detecting if fluid is being improperly supplied by the conduit means to the patient; and
    means responsive to the signal for detecting if fluid is being improperly supplied by the conduit means to the patient.

2. An infusion system as recited in claim 1, wherein the fluid-delivery means includes a gravity-fed infusion arrangement.

3. An infusion system as recited in claim 1, wherein the fluid-delivery means includes a flow control device.

4. An infusion system as recited in claim 3, wherein the flow control device includes an infusion pump.

5. An infusion system as recited in claim 1, wherein the signal has a waveform and the identification means includes microprocessor means for examining the waveform of the signal under program control.

6. An infusion system as recited in claim 5, wherein:
    the microprocessor means includes means responsive to the signal for determining a baseline pressure of the pressure in the fluid-delivery means; and
    the microprocessor means is responsive to a fluctuation in the baseline pressure exceeding a predefined threshold.

7. An infusion system as recited in claim 6, wherein the baseline pressure is determined according to the relationship:

$$B = B_1 + K(B_2)$$

where B is the baseline pressure being determined, $B_1$ is the baseline pressure at an instant prior to the determination, K is a constant, and $B_2$ is the rms value of a plurality of segments of the baseline pressure prior to the determination.

8. An infusion system as recited in claim 5, wherein the microprocessor means is responsive to the amplitude of the signal exceeding a predefined threshold.

9. An infusion system as recited in claim 5, wherein:
    the fluid-delivery means causes pressure changes; and
    the microprocessor means includes means for identifying pressure artifacts characteristic of patient activity amidst pressure changes caused by the fluid-delivery means.

10. An infusion system as recited in claim 9, wherein the microprocessor means is responsive to the waveform of the signal having a periodic pattern characteristic of the fluid-delivery means.

11. An infusion system as recited in claim 9, wherein the microprocessor means is responsive to the number of zero crossings of the signal exceeding a predefined number.

12. An infusion system as recited in claim 9, wherein the microprocessor means is responsive to the waveform of the signal having a repeating pattern occurring at regular intervals.

13. An infusion system as recited in claim 9, wherein the microprocessor means is responsive to the waveform of the signal having an average amplitude exceeding a predefined value.

14. An infusion system as recited in claim 1, further comprising alarm means responsive to the signal for producing a human sensible signal as an indication of patient activity.

15. An infusion system, comprising:
    fluid-delivery means for delivering a fluid from a separate source of the fluid into a patient, the fluid-delivery means including an infusion device for delivering the fluid and conduit means for conducting the fluid from the infusion device to the patient;
    transducer means for producing a signal related to the pressure of the fluid in the conduit means;
    identification means responsive to the signal for ascertaining if the level of patient activity is suitable for detecting if fluid is being improperly supplied by the conduit means to the patient; and
    means responsive to the signal for detecting if fluid is being improperly supplied by the conduit to the patient.

16. An infusion system for infusing a fluid into a patient comprising:
    an infusion device for delivering the fluid, said infusion device including means for delivering the fluid in a normal delivery pattern and for delivering a test pulse of the fluid with the test pulse being distinguishable from the normal delivery pattern;

conduit means for conducting the fluid from the infusion device to the patient, said test pulse creating a pressure wave response in the conduit means;

first means responsive to the pressure of the fluid in the conduit means during delivery in a normal delivery pattern to ascertain if the level of patient activity is suitable for detecting if fluid is being improperly supplied by the conduit means to the patient; and means responsive to the pressure wave response for detecting if fluid is being improperly supplied by the conduit means to the patient.

17. An apparatus for determining if fluid is being properly supplied through a fluid delivery system to a patient, said apparatus comprising:

means for delivering fluid through the delivery system so as to create a pressure wave response in the delivery system;

first means responsive to the pressure in the delivery system to ascertain if the level of patient activity is suitable for detecting if fluid is being improperly supplied by the delivery system to the patient; and means responsive to the pressure wave response for detecting if fluid is being improperly supplied by the delivery system to the patient.

18. A method of detecting an abnormal infusion condition, comprising:

infusing a fluid into a patient through a conduit, with the pressure of the fluid in the conduit being subject to being influenced by certain patient activity;

monitoring the fluid pressure in the conduit in order to detect pressure artifacts characteristic of patient activity; and performing a site check for abnormal infusion conditions at a time when no such pressure artifacts are detected.

19. A method as recited in claim 18, wherein the step of performing a site check includes:

delivering a test pulse of the fluid through the conduit into the patient to create a pressure wave response in the conduit; and monitoring the pressure wave response in the conduit in order to identify a waveform characteristic of an abnormal infusion condition.

20. A method as recited in claim 18, wherein the step of monitoring includes providing a signal having a waveform which is related to the fluid pressure in the conduit and examining the waveform of the signal under program control.

21. A method as recited in claim 20, wherein the step of monitoring includes comparing the magnitude of the signal with a predefined threshold.

22. A method as recited in claim 20, wherein:

the step of infusing includes providing a fluid-delivery means for infusing the fluid into the patient through the conduit, the fluid-delivery means causing pressure changes in the conduit; and the step of monitoring includes identifying pressure artifacts characteristic of patient activity amidst pressure changes caused by the fluid-delivery means.

23. A method as recited in claim 22, wherein the step of monitoring includes comparing the signal to a predetermined periodic pattern characteristic of the fluid-delivery means.

24. A method as recited in claim 22, wherein the step of monitoring includes comparing the number of zero crossings of the signal to a predefined number.

25. A method as recited in claim 22, wherein the step of monitoring includes comparing the interval between repetitive patterns of the signal to a predefined number.

26. A method of detecting an abnormal infusion condition, comprising:

infusing a fluid into a patient through a conduit with the pressure of the fluid in the conduit being subject to being influenced by certain patient activity;

monitoring the fluid pressure in the conduit in order to detect pressure artifacts characteristic of patient activity; and performing a site check for abnormal infusion conditions at a time when such pressure artifacts indicate that the level of patient activity is suitable for performing said site check.

27. An infusion system, comprising:

fluid-delivery means for delivering a fluid from a separate source of the fluid into a patient;

transducer means for producing a signal related to the pressure of the fluid in the fluid-delivery means;

identification means responsive to the signal for identifying pressure artifacts characteristic of patient activity;

the signal having a waveform and the identification means including microprocessor means for examining the waveform of the signal under program control;

the microprocessor means including means responsive to the signal for determining a baseline pressure of the pressure in the fluid-delivery means;

the microprocessor means being responsive to a fluctuation in the baseline pressure exceeding a predefined threshold; and the baseline pressure being determined according to the relationship:

$$B = B_1 + K(B_2)$$

where B is the baseline pressure being determined, $B_1$ is the baseline pressure at an instant prior to the determination, K is a constant, and $B_2$ is the rms value of a plurality of segments of the baseline pressure prior to the determination.

* * * * *